United States Patent [19]

O'Brien et al.

[11] Patent Number: 5,756,545
[45] Date of Patent: May 26, 1998

[54] BIPHENYSULFONAMIDE MATRIX METAL ALLOPROTEINASE INHIBITORS

[75] Inventors: Patrick Michael O'Brien, Stockbridge; Drago Robert Sliskovic, Saline, both of Mich.

[73] Assignee: Warner-Lambert Company, Morris Plains, N.J.

[21] Appl. No.: 844,598

[22] Filed: Apr. 21, 1997

[51] Int. Cl.⁶ .................................................. A61K 31/20
[52] U.S. Cl. .......................... 514/562; 514/539; 560/12; 562/430
[58] Field of Search ............................. 560/12; 562/430; 514/562, 539

[56] References Cited

U.S. PATENT DOCUMENTS

| | | |
|---|---|---|
| 3,784,701 | 1/1974 | Tomcufcik et al. |
| 4,269,775 | 5/1981 | Szczepanski et al. |
| 4,388,464 | 6/1983 | Kristinsson et al. |
| 4,599,361 | 7/1986 | Dickens et al. ............ 514/575 |
| 4,632,931 | 12/1986 | Nakane et al. ............ 514/382 |
| 4,715,883 | 12/1987 | Lukaszczyk et al. |
| 5,270,326 | 12/1993 | Galardy et al. ............ 514/323 |

FOREIGN PATENT DOCUMENTS

| | | |
|---|---|---|
| 0 305 947 A1 | 3/1989 | European Pat. Off. |
| 0 548 798 A1 | 6/1993 | European Pat. Off. |
| 0 606 046 A1 | 7/1994 | European Pat. Off. |
| WO 94/12181 | 11/1993 | WIPO |
| WO 95/13289 | 11/1994 | WIPO |
| WO 95/35275 | 5/1995 | WIPO |
| WO 95/35276 | 6/1995 | WIPO |
| WO 96/00214 | 6/1995 | WIPO |
| WO 96/11209 | 10/1995 | WIPO |
| WO 96/15096 | 11/1995 | WIPO |
| 97/27174 | 7/1997 | WIPO |

OTHER PUBLICATIONS

Biochemistry, vol. 31, No. 45, 1992, Qi–Zhuang Ye, et al., pp. 11231–11235.

J. Med. Chem, 1993, vol. 36, No. 26, Chapman et al., pp. 4293–4301.

*Primary Examiner*—Samuel Barts
*Attorney, Agent, or Firm*—Charles W. Ashbrook

[57] ABSTRACT

Compounds of the formula

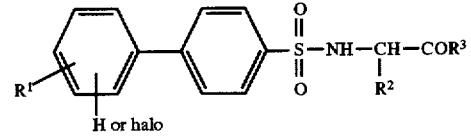

wherein $R^1$ includes alkyl, halo, nitro, amino, cyano, alkoxy, and alkoxycarbonyl; $R^2$ is alkyl and substituted alkyl; and $R^3$ is OH or NHOH are useful for inhibiting matrix metalloproteinase enzymes in animals, and as such, prevent and treat diseases resulting from the breakdown of connective tissues.

18 Claims, No Drawings

BIPHENYSULFONAMIDE MATRIX METAL ALLOPROTEINASE INHIBITORS

FIELD OF THE INVENTION

This invention relates to a group of biphenylsulfonamides which inhibit matrix metalloproteinase enzymes and thus are useful for treating diseases resulting from tissue breakdown, such as arthritis, atherosclerosis, restenosis, and osteoporosis.

BACKGROUND OF THE INVENTION

Matrix metalloproteinases are naturally occurring enzymes found in most mammals and are associated with the breakdown of connective tissues. The class includes gelatinase A and B, stromelysin-1, fibroblast collagenase, neutrophil collagenase, matrilysin, and other forms of collagenase. These enzymes have been implicated with a number of diseases which result from breakdown of connective tissue, such as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these diseases is now recognized to be by inhibiting metalloproteinase enzymes, thereby curtailing and eliminating the breakdown of connective tissues that results in the disease states.

Several inhibitors of metalloproteinases have been identified. Many inhibitors are complex peptides, for instance as described by Chapman, et al., in *J. Med. Chem.*, 1993;36:4293–4301. Small peptide inhibitors are also known, for example as described in U.S. Pat. Nos. 4,599,361 and 5,270,326 as well as non-peptide as in WO 95/35276.

The need continues for small molecular weight molecules which can be economically prepared and yet are effective inhibitors of metalloproteinases. We have now discovered a group of biphenylsulfonamides which have exceptionally good inhibitory activity. An object of this invention is to provide such compounds, their pharmaceutical formulations, and a method for using them to treat diseases mediated by metalloproteinases.

SUMMARY OF THE INVENTION

This invention provides biphenylsulfonamides which are inhibitors of metalloproteinases. The invention compounds have Formula I

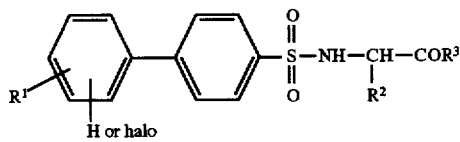

wherein:
$R^1$ is $C_1$–$C_6$ alkyl, halo, nitro, $(CH2)_{0-4}$—$NR^4R^5$, cyano, $OR^4$,

$R^2$ is hydrogen or $C_1$–$C_6$ alkyl, optionally substituted by the following groups:
phenyl, substituted phenyl, phenoxy, substituted phenoxy, $NR^4R^5$, $OR^6$, carboxy, carboxamido,

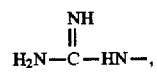

thio, methylthio, indole, imidazole, and phthalimido;
$R^3$ is OH, O $C_1$–$C_6$ alkyl, or NHOH;
$R^4$ is hydrogen, $C_1$–$C_6$ alkyl, or $C_1$–$C_6$ alkanoyl;
$R^5$ is hydrogen or $C_1$–$C_6$ alkyl; and
$R^6$ is hydrogen, $C_1$–$C_6$ alkyl, $C_1$–$C_6$ alkanoyl, phenyl, or substituted phenyl; and pharmaceutically acceptable salts and solvates thereof.

Preferred compounds are those wherein $R^1$ is halo, and $R^3$ is OH.

Additionally preferred are compounds are those wherein $R^2$ is $C_1$–$C_6$ alkyl.

Especially preferred compounds have Formula II

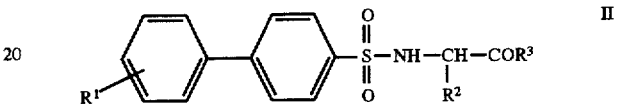

wherein:
$R^1$ is $C_1$–$C_6$ alkyl, halo, nitro, $NR^4R^5$, cyano, $OR^4$, and $COOR^4$;
$R^2$ is $C_1$–$C_6$ alkyl, optionally substituted by phenyl, substituted phenyl, $NR^4R^5$, $OR^6$, carboxy, carboxamido,

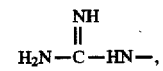

thio, methylthio, indole, imidazole, and phthalimido;
$R^3$ is OH, $OC_1$–$C_6$ alkyl, or NHOH;
$R^4$ is hydrogen, $C_1$–$C_6$ alkyl, or $C_1$–$C_6$ alkanoyl;
$R^5$ is hydrogen or $C_1$–$C_6$ alkyl; and
$R^6$ is hydrogen, $C_1$–$C_6$ alkyl, $C_1$–$C_6$ alkanoyl, phenyl, or substituted phenyl.

The most preferred compounds are those wherein $R^1$ is at the 4'-position of the biphenyl ring system, and especially where $R^1$ is bromo.

A further embodiment of the invention is a pharmaceutical formulation comprising a compound of Formula I admixed with a diluent, carrier, or excipient therefor.

The invention also provides a method for inhibiting the action of a matrix metalloproteinase enzyme in a mammal comprising administering a matrix metalloproteinase inhibiting amount of a compound of Formula I.

DETAILED DESCRIPTION OF THE INVENTION

In the formula defining the invention compounds, $R^1$ includes halo, which term refers to fluoro, chloro, bromo, and iodo, with chloro and bromo being preferred, and bromo being most preferred.

The term "$C_1$–$C_6$ alkyl" means straight and branched aliphatic groups having from 1 to 6 carbon atoms, examples of which include methyl, ethyl, isopropyl, tert.-butyl, n-hexyl, and isohexyl. The $R^2$ alkyl group can be substituted with phenyl, e.g., benzyl, 3-phenylpropyl; or substituted phenyl, which term refers to phenyl substituted with one, two, or three groups independently selected from the groups defined by $R^1$. Typical substituted phenyl groups thus include 2-chlorophenyl, 2,3-dibromophenyl, 3-nitrophenyl, 4-hydroxyphenyl, 3-bromo-4-hydroxyphenyl, 2-dimethylaminophenyl, 4-tert-butoxyphenyl, 2,3,5-trifluorophenyl, and the like. The $R^2$ alkyl group can also be substituted with groups such as hydroxy, alkoxy, alkanoyloxy, phenoxy, substituted phenoxy, amino, carboxy, thio, and the like. Typical substituted alkyl groups include hydroxymethyl, methoxymethyl, 1-hydroxyethyl, 1-acetoxyethyl, 4-aminobutyl, 3-(4-chlorophenoxy)-hexyl, 4-(2-dimethylaminophenoxy)-butyl, 3-thiopropyl, 1-hydroxy-3-aminopropyl, and the like.

$R^3$ in Formula I means hydroxy, $C_1$–$C_6$ alkoxy, or NHOH.

The $R^1$ substituent can be $NR^4R^5$, where $R^4$ can be hydrogen, $C_1$–$C_6$ alkyl, or $C_1$–$C_6$ alkanoyl such as formyl, acetyl, propionyl, pivaloyl, and the like. Similarly, $R^5$ can be hydrogen or $C_1$–$C_6$ alkyl. Typical $NR^4R^5$ groups thus include amino, methylamino, diethylamino, acetamido, N-methylacetamido, and the like.

The invention includes pharmaceutically acceptable salts, for example salts of the acids when $R^3$ is OH. Such salts include those made by reaction of the acid with organic and inorganic bases such as diethylamine, benzylamine, sodium hydroxide, potassium hydroxide, and calcium hydroxide. The invention compounds of Formula I can also exist as hydrates and solvates, for example alcoholates such as ethanolate.

The invention compounds are prepared by methods commonly utilized in the art of organic synthesis. For example, a biphenylsulfonic acid, which is activated with a leaving group, such as a halogen or active ester, readily reacts with an amino acid ester according to the following general scheme:

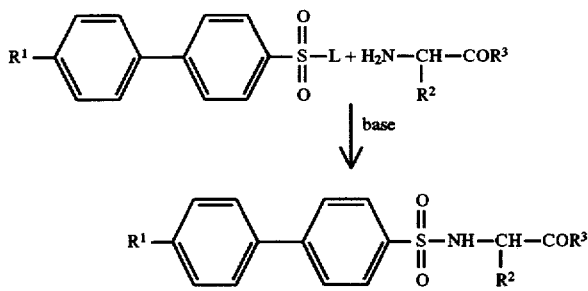

where L is a leaving group such as halo (e.g., chloro or bromo) or an active ester (e.g., pentachlorophenyloxy), $R^1$ and $R^2$ are as defined above, and $R^3$ is alkoxy such as tert.-butoxy. The sulfonyl halides are preferred starting materials, and these are readily prepared by reacting a substituted biphenyl compound, for example

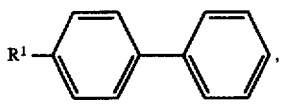

with chlorosulfonic acid to produce the corresponding biphenylsulfonic acid, followed by reaction of the biphenylsulfonic acid with a halogenating agent such as phosphorous oxychloride, oxalyl chloride, or the like. The resulting biphenyl sulfonyl halide is next reacted with an aminoacid ester to give an invention compound. This latter reaction typically is accomplished by mixing approximately equimolar quantities of the biphenylsulfonyl halide or active ester and aminoacid ester in a mutual unreactive solvent such as dichloromethane, chloroform, xylene, or the like. A base can be utilized, if desired, to act as an acid scavenger. Typical bases include triethylamine, N-methylmorpholine, and the like. The reaction generally is substantially complete within about 12 to 24 hours when carried out at a temperature of about 10° C. to about 50° C. The product, a biphenylsulfonamide ester of the invention, is readily isolated by removing the reaction solvent, for instance by evaporation under reduced pressure. The product can be further purified, if desired, by standard techniques such as chromatography, for instance over solid supports such as silica gel, or crystallization from solvents such as methanol, diethyl ether, and the like.

The preferred amino acid esters to be utilized in the above reaction are lower $C_1$–$C_6$ alkyl esters of the naturally occurring amino acids which are constituents of proteins. Typical amino acids thus include glycine, alanine, valine, leucine, isoleucine, phenylalanine, serine, cysteine, threonine, lysine, arginine, aspartic acid, asparagine, glutamic acid, glutamine, tyrosine, methionine, tryptophan, and histidine.

The esters, compounds of Formula I wherein $R^3$ is $C_1$–$C_6$ alkoxy, are useful intermediates to the acids and hydroxamic acids, in that they are readily hydrolyzed to the corresponding carboxylic acids by routine methods, for instance by reaction with a strong acid such as trifluoroacetic acid, polyphosphoric acid, sulfuric acid, or a strong base such as sodium hydroxide. The hydrolysis generally is carried out at a temperature of about 0° C. to about 25° C., and normally is complete within about 2 to 24 hours. The product, a compound of Formula I wherein $R^3$ is OH, can be isolated by diluting the reaction mixture with water and extracting the product into a water immiscible solvent such as ethyl acetate, dichloromethane, or the like, and then removing the organic solvent, for example by evaporation under reduced pressure. The free carboxylic acids thus formed can be converted to salts by reaction with a base such as sodium hydroxide, calcium carbonate, or the like. The carboxylic acids also can be reacted with hydroxylamine hydrochloride to form the corresponding hydroxamic acids, ie, compounds of Formula I where $R^3$ is NHOH.

An alternative method for preparing invention compounds of Formula I comprises reacting a 4-bromo or 4-iodo-benzene sulfonamide with a substituted benzene boronic acid according to the following scheme:

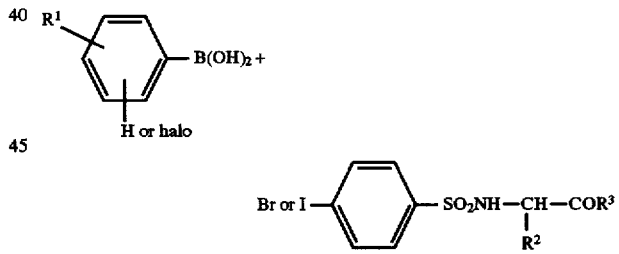

wherein $R^1$ and $R^2$ are as defined above, and $R^3$ preferably is alkyl. The coupling reaction is catalyzed by palladium, and generally is carried out aqueous sodium carbonate, and in a suitable solvent, for instance toluene or N,N-dimethylformamide. The coupling reaction generally is substantially complete within about 2 to 24 hours when carried out at a temperature of about 50° C. to 120° C. The product biphenyl sulfonamide is readily isolated by pouring the reaction mixture into an aqueous acid such as dilute HCl, and extracting it into a water immiscible solvent such as ethyl acetate or dichloromethane. The organic solution is separated and the solvent is removed by evaporation under reduced pressure to afford the invention compound of Formula I, which can be further purified, if desired, by normal methods such as crystallization and chromatography. The esters, where $R^3$ is alkyl, are readily hydrolized to the corresponding acid by standard methods.

The invention compounds contain at least one asymmetric carbon atom, and as such exist as optically active isomers. The invention contemplates the racemic forms as well as the individual isomers. The individual isomers can be prepared from optically pure starting materials, for example by utilizing naturally occurring amino acids, or by resolving the racemate by normal techniques such as chromatography and the like.

In a preferred embodiment, the invention compounds have the (S) configuration corresponding to naturally occurring amino acids from which they are derived.

The synthesis of typical biphenylsulfonamides of Formula I is illustrated by the following examples. The examples are representative only, and are not intended to be limiting in any respect.

EXAMPLE 1

(S)-2-(4'-Bromo-biphenyl-4-sulfonylamino)-3-methyl-butyric Acid

Step (a): 4'-Bromobiphenyl-4-sulfonic Acid

To a stirred solution of 4-bromobiphenyl (50 g, 0.21 mol) in chloroform (200 mL) was added dropwise at room temperature chlorosulfonic acid (32.5 g, 0.28 mol). The solution was stirred at room temperature for 16 hours, then diluted with hexanes (200 mL). The precipitate was collected by filtration and washed with hexanes to give 4'-bromobiphenyl-4-sulfonic acid (52.3 g, 79%) as a white solid. The crude product was used in the next step without further characterization.

Step (b): 4'-Bromobiphenyl-4-sulfonyl Chloride

The crude sulfonic acid (a) (52.3 g, 0.16 mol) was suspended in phosphorous oxychloride (200 mL) and refluxed for 64 hours. The solution was cooled to room temperature, filtered, and the filtrate was concentrated in vacuo leaving a brown solid (47 g). The crude product was purified utilizing silica gel chromatography (elution with hexanes/ethyl acetate (1:1)) to give the title compound (38.3 g, 69%) as a pale yellow solid.

$^1$HNMR (CDCl$_3$): δ 8.1 (d, 2H), 7.7 (d, 2H), 7.6 (d, 2H), 7.5 (d, 2H) ppm.

Step (c): (S)-2-(4'-Bromo-biphenyl-4-sulfonylamino)-3-methyl-butyric Acid Tert-butyl Ester To a solution of L-valine-tert-butyl ester hydrochloride (15.7 g, 0.075 mol) and N-methylmorpholine (15.2 g, 0.15 mol) in dichloromethane (250 mL) was added in one portion 4'-bromobiphenyl-4-sulfonyl chloride (25 g, 0.075 mol). The solution was stirred at room temperature for 16 hours, filtered, and the filtrate was concentrated in vacuo. The residue was diluted with ethyl acetate (250 mL) and washed with HCl (1N), saturated sodium chloride, and dried over magnesium sulfate. The drying agent was filtered, and the filtrate was concentrated in vacuo leaving a cream-colored solid. The crude product was purified using silica gel chromatography (elution with chloroform) to give the title compound (21.2 g, 60%) as a white solid.

$^1$HNMR (CDCl$_3$): δ 7.9 (d, 2H), 7.6 (dd, 4H), 7.4 (d, 2H) 5.1 (d, 1H), 3.6 (dd, 1H), 2.0 (m, 1H), 1.2 (s, 9H), 1.0 (d, 3H), 0.8 (d, 3H) ppm.

Step (d): (S)-2-(4'-Bromo-biphenyl-4-sulfonylamino)-3-methyl-butyric Acid

To a solution of anisole (4.9 g, 0.045 mol) in trifluoroacetic acid (200 mL) was added in small portions the tert-butyl ester (21.1 g) prepared in Step (c). The solution was stirred at room temperature for 16 hours, then poured over ice. The aqueous suspension was diluted with chloroform, the layers separated, and the organic portion was washed with saturated sodium chloride, dried (MgSO$_4$) and concentrated to dryness. The resulting solid was suspended in hexanes/diethyl ether (9:1) and collected by filtration to give the title compound (17.7 g, 96%) as a white solid, mp 192°–193° C.

$^1$HNMR (CDCl$_3$): δ 7.8 (d, 2H), 7.6 (d, 2H), 7.5 (d, 2H), 7.4 (d, 2H), 5.6 (d, 1H), 3.6 (dd, 1H), 2.0 (m, 1H), 0.9 (d, 3H), 0.7 (d, 3H) ppm.

Following the general procedure of Example 1, the following compounds were obtained:

EXAMPLE 2

(S)-2-(4'-Chloro-biphenyl-4-sulfonylamino)-3-methyl-butyric Acid mp 187°–188° C.;

$^1$HNMR (CDCl$_3$): δ 7.9 (d, 2H), 7.6 (d, 2H), 7.5 (d, 2H), 7.4 (d, 2H), 5.4 (d, 2H), 3.7 (dd, 1H), 2.0 (m, 1H), 0.9 (d, 3H), 0.8 (d, 3H) ppm.

EXAMPLE 3

(S)-3-Methyl-2-(4'-nitro-biphenyl-4-sulfonylamino)-butyric Acid $^1$HNMR (CDCl$_3$): δ 8.3 (d, 2H), 7.9 (d, 2H), 7.7 (d, 2H), 7.6 (d, 2H), 5.8 (d, 1H), 3.6 (dd, 1H), 2.0 (m, 1H), 0.9 (d, 3H), 0.7 (d, 3H) ppm.

EXAMPLE 4

(S)-2-(4'-Amino-biphenyl-4-sulfonylamino)-3-methyl-butyric Acid $^1$HNMR (CDCl$_3$): δ 7.6 (d, 2H), 7.4 (d, 2H), 7.2 (d, 2H), 6.5 (d, 2H), 5.8 (d, 1H), 3.5 (dd, 1H), 1.8 (m, 1H), 1.8 (d, 3H), 0.6 (d, 2H) ppm.

EXAMPLE 5

(S)-2-(4'-Cyano-biphenyl-4-sulfonylamino)-3-methyl-butyric Acid mp 182°–184° C.;

$^1$HNMR (CDCl$_3$): δ 7.9 (d, 2H), 7.7 (d, 2H), 7.6 (m, 4H), 5.8 (d, 1H), 3.6 (dd, 1H), 2.0 (m, 1H), 0.9 (d, 3H), 0.7 (d, 3H) ppm.

EXAMPLE 6

(S)-2-(3',4'-Dibromo-biphenyl-4-sulfonylamino)-3-methyl-butyric Acid, Sodium Salt

EXAMPLE 7

(S)-2-(3'-Bromo-biphenyl-4-sulfonylamino)-3-methyl-butyric Acid $^1$HNMR (CDCl$_3$): δ 7.8 (d, 2H), 7.7 (s, 1H), 7.6 (d, 2H), 7.5 (m, 2H), 7.3 (t, 1H), 5.0 (d, 1H), 3.8 (dd, 1H), 2.0 (m, 1H), 0.9 (d, 3H), 0.8 (d, 3H) ppm.

EXAMPLE 8

(S)-2-(4'-Bromo-2'-fluoro-biphenyl-4-sulfonylamino)-3-methyl-butyric Acid mp 175°–177° C.;

$^1$HNMR (DMSO-d$_6$): δ 8.1 (d, 1H), 7.8 (d, 2H), 7.7 (m, 3H), 7.5 (m, 2H), 3.5 (m, 1H), 1.9 (m, 1H), 0.7 (dd, 1H) ppm.

EXAMPLE 9

(R)-2-(4'-Bromo-biphenyl-4-sulfonylamino)-3-methyl-butyric Acid mp 191°–193° C.;

$^1$HNMR (CDCl$_3$): δ 7.9 (d, 2H), 7.6 (d, 2H), 7.5 (d, 2H), 7.4 (d, 2H), 5.5 (d, 1H), 3.7 (m, 1H), 2.0 (m, 1H), 0.9 (d, 3H), 0.8 (d, 2H) ppm.

When in the general procedure in Example 1 an appropriate amount of the tert.-butyl esters of L-phenylalanine, glycine, L-alanine, and L-leucine were substituted for L-valine-tert-butyl ester hydrochloride, the following compounds were obtained.

EXAMPLE 10
(S)-2-(4'-Bromo-biphenyl-4-sulfonylamino)-3-phenyl-propionic Acid
mp 159°–161° C.;
¹HNMR (CDCl₃): δ 7.7 (d, 2H), 7.5 (m, 4H), 7.4 (d, 2H), 7.1 (m, 5H), 5.6 (d, 1H), 4.1 (m, 1H), 3.1–2.9 (m, 2H) ppm.

EXAMPLE 11
(S)-(4'-Isopropyl-biphenyl-4-sulfonylamino)-3-phenyl-propionic Acid

EXAMPLE 12
(4'-Bromo-biphenyl-4-sulfonylamino)-acetic Acid
mp 200°–202° C.;
¹HNMR (CDCl₃): δ 7.7 (d, 2H), 7.4 (d, 2H), 7.3 (d, 2H), 7.2 (d, 2H), 6.8 (m, 1H), 3.4 (d, 2H) ppm.

EXAMPLE 13
(S)-2-(4'-Bromo-biphenyl-4-sulfonylamino)-propionic Acid
mp 195°–196° C.;
¹HNMR (CDCl₃): δ 7.7 (d, 2H), 7.4 (d, 2H), 7.3 (d, 2H), 7.2 (d, 2H), 6.6 (d, 2H), 3.7 (m, 1H), 1.1 (d, 3H) ppm.

EXAMPLE 14
(S)-2-(4'-Bromo-biphenyl-4-sulfonylamino)-4-methyl-pentanoic Acid
¹HNMR (CDCl₃): δ 7.9 (d, 2H), 7.6 (m, 4H), 7.4 (d, 2H), 5.1 (d, 1H), 3.9 (m, 1H), 1.7 (m, 1H), 1.4 (m, 2H), 1.9 (d, 3H), 1.7 (d, 3H) ppm.

The biphenylsulfonamides of Formula I can alternatively be prepared utilizing the following synthetic conditions:

EXAMPLE 15
(S)-2-(4'-Methoxy-biphenyl-4-sulfonylamino)-3-methyl-butyric Acid Step (a): 2-(4-Bromo-benzenesulfonylamino)-3-methyl-butyric Acid Tert-butyl Ester To a solution of 4-bromobenzenesulfonyl chloride (20 g, 0.070 mol) and (L)-valine-tert-butyl ester, hydrochloride (16.4 g, 0.078 mol) in aqueous tetrahydrofuran (400 mL, 1:1) was added dropwise triethylamine (15.6 g, 0.15 mol). The reaction mixture was stirred at room temperature for 16 hours, then diluted with aqueous HCl (1M, 300 mL) and ethyl acetate (300 mL). The layers were separated and the organic portion was washed with brine, dried (MgSO₄), filtered, and the filtrate was concentrated in vacuo leaving a white solid. The crude product was recrystallized from hexane/ethyl acetate to give the title compound as white crystalline needles. Yield: 19.7 g (67%); mp 108°–110°;
¹HNMR (CDCl₃): δ 7.7 (d, 4H), 7.6 (d, 4H), 5.1 (d, 1H), 3.6 (m, 1H), 2.0 (m, 1H), 1.2 (s, 9H), 0.9 (d, 3H), 0.8 (d, 3H) ppm.

Step (b): 2-(4'-Methoxy-biphenyl-4-sulfonylamino)-3-methyl-butyric Acid Tert-butyl Ester A solution of the 4-bromobenzenesulfonamide derivative (1 g, 2.64 mmol) prepared in Step (a) and 4-methoxybenzeneboronic acid (0.48 g, 3.17 mmol) in toluene (10 mL) was treated with tetrakis(triphenylphosphine)palladium(0) (0.15 g, 0.1 mmol) and aqueous sodium carbonate (0.5 g/5 mL H₂O), respectively. The reaction mixture was refluxed for 3 hours, then cooled to room temperature. Ethyl acetate (25 mL) and aqueous HCl (1M, 25 mL) were added, the layers separated, and the organic portion was dried (MgSO₄), filtered, and the filtrate was concentrated in vacuo. The resulting solid was triturated with hexane/ethyl acetate (3:1) and was collected by filtration. Yield: 0.68 g (62%);
¹HNMR (CDCl₃): δ 7.8 (d, 2H), 7.6 (d, 2H), 7.5 (d, 2H), 6.9 (d, 2H), 5.1 (d, 1H), 3.8 (s, 3H), 3.6 (m, 1H), 2.0 (m, 1H), 1.1 (s, 9H), 1.0 (d, 3H), 0.8 (d, 3H) ppm.

Step (c): The biphenyl derivative (0.67 g, 1.6 mmol) prepared in (b) was added to a solution of anisole (0.17 g, 1.6 mmol) in trifluoroacetic acid (10 mL). The solution was stirred at room temperature for 3 hours, then poured over ice. The product was partitioned between ethyl acetate and the aqueous acid, and the organic phase was separated, washed with brine, dried (MgSO₄), and concentrated in vacuo. The crude product was triturated with hexane/ethyl acetate (3:1) and collected by filtration to give the title compound (0.44 g, 77%) as a white solid, mp 180°–181° C.;
¹HNMR (DMSO-d₆): δ 8.0 (d, 1H), 7.7 (s, 4H), 7.6 (d, 2H), 7.0 (d, 2H), 3.8 (s, 3H), 3.5 (m, 1H), 1.9 (m, 1H), 0.7 (dd, 6H) ppm.

By substituting an appropriately substituted benzeneboronic acid derivative for 4-methoxybenzeneboronic acid in Step (b), the following compounds were prepared by the procedure of Example 15:

EXAMPLE 16
(S)-2-(4'-Fluoro-biphenyl-4-sulfonylamino)-3-methyl-butyric Acid
mp 165°–166° C.;
¹HNMR (DMSO-d₆): δ 8.0 (d, 1H), 7.7 (m, 6H), 7.3 (m, 2H), 3.5 (, 1H), 1.9 (m, 1H), 0.7 (dd, 6H) ppm.

EXAMPLE 17
(S)-2-(3'-Fluoro-biphenyl-4-sulfonylamino)-3-methyl-butyric Acid
mp 145°–147° C.;
¹HNMR (DMSO-d₆): δ 8.1 (bs, 1H), 7.9 (dd, 4H), 7.5 (m, 3H), 7.3 (t, 1H), 3.6 (m, 1H), 2.0 (m, 1H), 0.9 (dd, 6H) ppm.

EXAMPLE 18
(S)-3-Methyl-2-(4'-methyl-biphenyl-4-sulfonylamino)-butyric Acid
mp 185°–186° C.;
¹HNMR (DMSO-d₆): δ 8.0 (d, 1H), 7.8 (s, 4H), 7.6 (d, 2H), 7.3 (d, 2H), 3.5 (m, 1H), 2.5 (s, 3H), 1.9 (m, 1H), 0.7 (dd, 6H) ppm.

EXAMPLE 19
(S)-3-Methyl-2-(4'-trifluoromethyl-biphenyl-4-sulfonylamino)-butyric Acid
mp 183°–184° C.;
¹HNMR (DMSO-d₆): δ 8.1 (bs, 1H), 7.9 (m, 4H), 7.8 (m, 4H), 3.5 (m, 1H), 1.8 (m, 1H), 0.8 (dd, 6H) ppm.

EXAMPLE 20
2-(4'-Formyl-biphenyl-4-sulfonylamino)-3-methyl-butyric Acid
mp 189° C., dec;
¹HNMR (CDCl₃): δ 10.0 (s, 1H), 7.9 (m, 4H), 7.6 (m, 4H), 5.8 (d, 1H), 3.6 (m, 1H), 2.0 (m, 1H), 0.9 (d, 3H), 0.7 (d, 2H) ppm.

EXAMPLE 21
4'-(1-Carboxy-2-methyl-propylsulfamoyl)-biphenyl-4-carboxylic Acid

EXAMPLE 22
2-(4'-Hydroxymethyl-biphenyl-4-sulfonylamino)-3-methyl-butyric Acid

EXAMPLE 23
2-(4'-Aminomethyl-biphenyl-4-sulfonylamino)-3-methyl-butyric Acid The invention compounds have been evaluated in standard in vitro assays and shown to be potent inhibitors of several matrix metalloproteinase enzymes. Specifically, the compounds have been evaluated for their ability to inhibit gelatinase A-catalyzed hydrolysis of thiopeptolide and gelatin, and the stromelysin-catalyzed hydrolysis of thiopeptolide. The compounds were evaluated at various concentrations in order to determine their respective $IC_{50}$, the micromolar concentration of compound required to cause a 50% inhibition of the hydrolytic activity of the respective enzymes.

Table I below presents inhibitory activity for representative invention compounds of Formula I. In the table, $G_ACD$ (T) refers to gelatinase A-catalytic domain hydrolysis of thiopeptolide substrate; $G_ACD$ (Gel) refers to gelatinase A-catalytic domain hydrolysis of gelatin substrate; SCD (T) refers to stromelysin catalytic domain hydrolysis of thiopeptolide.

TABLE I

| Compound of Example No. | ($IC_{50}$) μM | | |
|---|---|---|---|
| | $G_ACD$ (T) | $G_ACd$ (Gel) | SCD (T) |
| 1 | 0.005 | 0.025 | 0.012 |
| 2 | 0.013 | 0.061 | 0.100 |
| 3 | 0.087 | 0.200 | 0.031 |
| 4 | 0.044 | 0.188 | 0.067 |
| 5 | 0.032 | 0.157 | 0.009 |
| 7 | 0.731 | 1.300 | 0.347 |
| 8 | 0.006 | 0.019 | 0.030 |
| 9 | 0.017 | 0.190 | 0.011 |
| 10 | 0.026 | 0.045 | 0.026 |
| 12 | 0.021 | 0.079 | 0.060 |
| 13 | 0.019 | 0.022 | 0.028 |
| 14 | 0.015 | 0.029 | 0.013 |
| 15 | 0.002 | 0.014 | 0.008 |
| 16 | 0.051 | 0.094 | 0.014 |
| 17 | 0.067 | 0.371 | 0.027 |
| 18 | 0.002 | 0.005 | 0.012 |
| 19 | 0.008 | 0.075 | 0.014 |

The compounds were additionally evaluated for their ability to inhibit full-length collagenase hydrolysis of thiopeptolide substrate (FLC) and full-length gelatinase B (FLGB) hydrolysis of thiopeptolide. The results of representative compounds is given in Table II.

TABLE II

| Compound of Example No. | ($IC_{50}$) μM | |
|---|---|---|
| | FLC | FLGB |
| 1 | 3.24 | 8.34 |
| 2 | 7.5 | 23.0 |
| 7 | 13.2 | 30.0 |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg to about 100 mg per kilogram daily will be effective. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg, such that it will be an amount which is effective to treat the particular disease being prevented or controlled.

The following examples illustrate typical formulations provided by the invention.

EXAMPLE 24

| Tablet Formulation | |
|---|---|
| Ingredient | Amount (mg) |
| 2-(4'-bromobiphenyl-4-sulfonylamino)-3-methyl-butyric acid | 25 |
| Lactose | 50 |
| Corn starch (for mix) | 10 |
| Corn starch (paste) | 10 |
| Magnesium stearate (1%) | 5 |
| Total | 100 |

The biphenylsulfonamide, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

EXAMPLE 25

| Preparation for Oral Solution | |
|---|---|
| Ingredient | Amount |
| (R)-2-(4'-Cyanobiphenyl-4-sulfonylamino)-3-phenyl-propionic acid sodium salt | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the biphenylsulfonamide is dissolved therein. The saccharin, sodium benzoate, flavor, and dye are added and dissolved. The volume is adjusted to 100 mL with distilled water. Each milliliter of syrup contains 4 mg of invention compound.

EXAMPLE 26
Parenteral Solution

In a solution of 700 mL of propylene glycol and 200 mL of water for injection is suspended 20 g of (S)-2-(4'-amino-biphenyl-4-sulfonylamino)-3-(3-ethoxyphenyl)-propionic acid. After suspension is complete, the pH is adjusted to 6.5 with 1N sodium hydroxide, and the volume is made up to 1000 mL with water for injection. The formulation is sterilized, filled into 5.0 mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes.

What is claimed is:
1. A compound of the Formula I

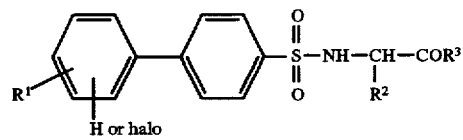

wherein:

$R^1$ is $C_1$–$C_6$ alkyl, halo, nitro, $(CH_2)_{0-4}$—$NR^4R^5$, cyano, $OR^4$,

$R^2$ is hydrogen or $C_1$–$C_6$ alkyl, optionally substituted by the following groups:
phenyl, substituted phenyl, phenoxy, substituted phenoxy, $NR^4R^5$, $OR^6$, carboxy, carboxamido,

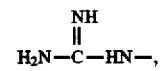

thio, methylthio, indole, imidazole, and phthalimido;
$R^3$ is OH, O $C_1$–$C_6$ alkyl, or NHOH;

$R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl, and pharmaceutically acceptable salts and solvates thereof.

2. A compound of claim 1 having the formula

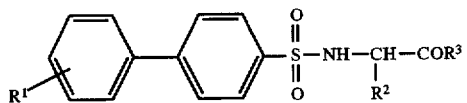

wherein:

$R^1$ is $C_1$–$C_6$ alkyl, halo, nitro, $NR^4R^5$, cyano, $OR^4$, and $COOR^4$;

$R^2$ is $C_1$–$C_6$ alkyl, optionally substituted by phenyl, substituted phenyl, $NR^4R^5$, $OR^6$, carboxy, carboxamido,

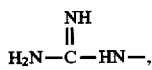

thio, methylthio, indole, imidazole, and phthalimido;

$R^3$ is OH, O $C_1$–$C_6$ alkyl, or NHOH;

$R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl.

3. A compound of claim 2 wherein $R^3$ is OH.

4. A compound of claim 3 wherein $R^2$ is $C_1$–$C_6$ alkyl.

5. A compound of claim 4 wherein $R^1$ is at the 4' position.

6. A compound of claim 1 which is selected from (S)-2-(4'-Bromo-biphenyl-4-sulfonylamino)-3-methyl-butyric acid;

(S)-2-(4'-Chloro-biphenyl-4-sulfonylamino)-3-methyl-butyric acid;

(S)-3-Methyl-2-(4'-nitro-biphenyl-4-sulfonylamino)-butyric acid;

(S)-2-(4'-Amino-biphenyl-4-sulfonylamino)-3-methyl-butyric acid;

(S)-2-(4'-Cyano-biphenyl-4-sulfonylamino)-3-methyl-butyric acid;

(S)-2-(3',4'-Dibromo-biphenyl-4-sulfonylamino)-3-methyl-butyric acid, sodium salt;

(S)-2-(3'-Bromo-biphenyl-4-sulfonylamino)-3-methyl-butyric acid (S)-2-(4'-Bromo-2'-fluoro-biphenyl-4-sulfonylamino)-3-methyl-butyric acid, (R)-2-(4'-Bromo-biphenyl-4-sulfonylamino)-3-methyl-butyric acid;

(S)-2-(4'-Bromo-biphenyl-4-sulfonylamino)-propionic acid;

(S)-2-(4'-Bromo-biphenyl-4-sulfonylamino)-4-methyl-pentanoic acid;

(S)-2-(4'-Methoxy-biphenyl-4-sulfonylamino)-3-methyl-butyric acid;

(S)-2-(4'-Fluoro-biphenyl-4-sulfonylamino)-3-methyl-butyric acid;

(S)-2-(3'-Fluoro-biphenyl-4-sulfonylamino)-3-methyl-butyric acid;

(S)-3-Methyl-2-(4'-trifluoromethyl-biphenyl-4-sulfonylamino)-butyric acid;

2-(4'-Formyl-biphenyl-4-sulfonylamino)-3-methyl-butyric acid;

4'-(1-Carboxy-2-methyl-propylsulfamoyl)-biphenyl-4-carboxylic acid;

2-(4'-Hydroxymethyl-biphenyl-4-sulfonylamino)-3-methyl-butyric acid; and 2-(4'-Aminomethyl-biphenyl-4-sulfonylamino)-3-methyl-butyric acid.

7. A compound of claim 2 wherein $R^2$ is $C_1$–$C_6$ alkyl substituted with phenyl or substituted phenyl.

8. A compound of claim 7 which is (S)-2-(4'-bromo-biphenyl-4-sulfonylamino)-3-phenyl-propionic acid, or (S)-(4'-isopropyl-biphenyl-4-sulfonylamino)-3-phenyl-propionic acid.

9. The compound which is (S)-2-(4'-bromo-biphenyl-4-sulfonylamino)-3-methyl-butyric acid.

10. A compound of claim 1 wherein $R^3$ is O $C_1$–$C_6$ alkyl.

11. A compound of claim 10 which is (S)-2-(4'-bromo-biphenyl-4-sulfonylamino)-3-methyl-butyric acid tert.-butyl ester.

12. A pharmaceutical formulation comprising a compound of claim 1 admixed with a diluent, carrier, or excipient therefor.

13. A pharmaceutical formulation comprising (S)-2-(4'-bromo-biphenyl-4-sulfonylamino)-3-methyl-butyric acid admixed with a diluent, carrier, or excipient therefor.

14. A method for inhibiting a matrix metalloproteinase enzyme by administering a matrix metalloproteinase inhibiting amount of a compound of claim 1.

15. A method for inhibiting a matrix metalloproteinase enzyme by administering a matrix metalloproteinase inhibiting amount of (S)-2-(4'-bromo-biphenyl-4-sulfonylamino)-3-methyl-butyric acid.

16. A method of treating arthritis comprising administering a matrix metalloproteinase inhibiting amount of a compound of claim 1.

17. A method of treating restenosis comprising administering a matrix metalloproteinase inhibiting amount of a compound of claim 1.

18. A method of treating atherosclerosis comprising administering a matrix metalloproteinase inhibiting amount of a compound of claim 1.

* * * * *